United States Patent
Cheng et al.

(10) Patent No.: US 6,489,529 B1
(45) Date of Patent: Dec. 3, 2002

(54) PRODUCTION OF MONOCYCLOALKYL AROMATIC COMPOUNDS

(75) Inventors: Jane C. Cheng, Voorhees, NJ (US); Jose G. Santiesteban, West Chester, PA (US); Michael A. Steckel, Media, PA (US); James C. Vartuli, West Chester, PA (US)

(73) Assignee: ExxonMobil Oil Corporation, Fairfax, VA (US)

( * ) Notice: Subject to any disclaimer, the term of this patent is extended or adjusted under 35 U.S.C. 154(b) by 0 days.

(21) Appl. No.: 09/490,435

(22) Filed: Jan. 24, 2000

(51) Int. Cl.⁷ ............................................. C07C 15/12
(52) U.S. Cl. ...................... 585/471; 585/475
(58) Field of Search .................. 585/475, 471

(56) References Cited

U.S. PATENT DOCUMENTS

| | | | |
|---|---|---|---|
| 3,308,069 A | 3/1967 | Wadlinger et al. | 252/455 |
| 3,766,093 A | 10/1973 | Chu | 252/455 |
| 3,956,183 A * | 5/1976 | Zuech | 502/74 |
| 3,984,490 A | 10/1976 | Chung et al. | 260/668 |
| 4,094,918 A | 6/1978 | Murtha et al. | 260/668 |
| 4,122,125 A | 10/1978 | Murtha et al. | 260/668 |
| 4,177,165 A | 12/1979 | Murtha et al. | 252/455 |
| 4,206,082 A | 6/1980 | Murtha et al. | 252/455 |
| 4,237,329 A | 12/1980 | Kamiyama et al. | |
| 4,439,409 A | 3/1984 | Puppe et al. | 423/328 |
| 4,826,667 A | 5/1989 | Zones et al. | 423/277 |
| 4,954,325 A | 9/1990 | Rubin et al. | 423/328 |
| 5,053,571 A | 10/1991 | Makkee | 585/425 |
| 5,236,575 A | 8/1993 | Bennett et al. | 208/46 |
| 5,250,277 A | 10/1993 | Kresge et al. | 423/329 |
| 5,362,697 A | 11/1994 | Fung et al. | 502/71 |
| 5,510,309 A * | 4/1996 | Chang et al. | 502/308 |
| 6,037,513 A * | 3/2000 | Chang et al. | 585/467 |

FOREIGN PATENT DOCUMENTS

| | | |
|---|---|---|
| EP | 0439632 | 8/1991 |
| EP | 0538518 | 4/1993 |
| WO | 95/07874 | 3/1995 |
| WO | 96/20148 | 7/1996 |

* cited by examiner

Primary Examiner—Thuan D. Dang
(74) Attorney, Agent, or Firm—Darryl M. Tyus

(57) ABSTRACT

There is described a process for the transalkylation of a polycycloalkyl aromatic compound, particularly the transalkylation of dicyclohexylbenzene to produce monocyclohexylbenzene. The process comprises contacting the polycycloalkyl aromatic compound with benzene in the presence of a catalyst selected from the group consisting of an acidic solid comprising a Group IVB metal oxide modified with an oxyanion of a Group VIBA metal oxide, TEA-mordenite, zeolite beta and a porous crystalline material having an X-ray diffraction pattern including d-spacing maxima at 12.4±0.25, 6.9±0.15, 3.57±0.07 and 3.42±0.07 Angstrom. Preferably the catalyst is a $WO_x/ZrO_2$ material.

9 Claims, No Drawings

PRODUCTION OF MONOCYCLOALKYL AROMATIC COMPOUNDS

FIELD OF INVENTION

This invention relates to a process for the production of monocycloalkyl aromatic compounds by transalkylation of polycycloalkyl aromatic compounds and in particular to a process for the production of monocyclohexylbenzene by transalkylation of dicyclohexylbenzene.

BACKGROUND TO THE INVENTION

Cyclohexylbenzene can be used to produce phenol, which is one of the most important industrial chemicals in the world. As of December 1995, more than 88% of world phenol capacity was based on cumene peroxidation with acetone coproduction. One of the primary economic difficulties of the cumene peroxidation route is that it requires the existence of an available market for the co-produced acetone. Currently, the growth of market demand for phenol exceeds that for acetone, and hence there exists an acetone oversupply problem. It is expected that this unbalanced growth will continue for some time.

Hydroperoxidation of cyclohexylbenzene (analogous to cumene peroxidation) could offer an alternative route for phenol production without the problem of acetone co-production. This alternative route co-produces cyclohexanone, which is a much more valuable and desirable by-product than acetone. Thus cyclohexanone is useful for the manufacture of caprolactam and nylon.

Dehydrogenation of cyclohexylbenzene also offers a low cost alternative to produce diphenyl from benzene. Diphenyl is used mainly for heat-transfer applications. Currently the main source of diphenyl is as a by-product (1 g diphenyl/100 g benzene) in benzene production by toluene dealkylation. The crude diphenyl is refined to 93–97% purity by distillation. High purity diphenyl can also be produced by direct thermal dehydrocondensation of benzene at 700–800° C. in gas or electrically heated tubular reactors. This process is energy intensive and produces by-products of terphenyl, higher polyphenyls and tars.

It is known that cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. More recently, U.S. Pat. No. 5,053,571 has proposed the use of ruthenium and nickel supported on zeolite beta as an aromatic hydroalkylation catalyst.

In our co-pending U.S. patent application Ser. No. 09/112,546 filed Jul. 9, 1998 we have described a process for the hydroalkylation of aromatic hydrocarbons over a catalyst comprising a hydrogenation metal and a crystalline inorganic oxide material having an X-ray diffraction pattern including d-spacing maxima at 12.4±0.25, 6.9±0.15, 3.57±0.07 and 3.42±0.07 Angstrom. Preferably the oxide material is MCM-22.

However, known methods for the hydroalkylation of benzene produce significant quantities of cyclohexane and dicyclohexylbenzene as byproducts. Cyclohexane can be readily recovered by dehydrogenation to benzene. However, there is need for an effective process for converting the dicyclohexylbenzene by-product to useful products, preferably the desired monocyclohexylbenzene. One possible solution is transalkylation of the dicyclohexylbenzene with benzene to form additional cyclohexylbenzene. To date, little work has been reported on dicyclohexylbenzene/ benzene transalkylation. Moreover, although certain catalysts, such as rare earth exchanged faujasite (U.S. Pat. No. 3,984,490), aluminum chloride and acid clay, have been proposed for this reaction, the existing catalysts suffer from significant shortcomings. Accordingly, a need exists for an improved process for the transalkylation of polycycloalkyl aromatic compounds to their monocycloalkyl analogs.

SUMMARY OF THE INVENTION

"According to the invention there is provided a process for the transalkylation of a polycycloalkyl aromatic compound comprising the step of contacting the polycycloalkyl aromatic compound with benzene in the presence of a catalyst selected from the group consisting of an acidic solid comprising a Group IVB metal oxide modified with an oxyanion of a Group VIB metal oxide, TEA-mordenite, zeolite beta and a porous crystalline material having an X-ray diffraction pattern including d-spacing maxima at 12.4±0.25, 6.9±0.15, 3.57±0.07 and 3.42±0.07 Angstrom."

Preferably, the polycycloalkyl aromatic compound is dicyclohexylbenzene.

"Preferably, said acidic solid is an oxide of zicronium modified with an oxyanion of trugsten."

Preferably, said porous crystalline material is MCM-22.

DETAILED DESCRIPTION OF THE INVENTION

"The present invention provides a process for the transalkylation of a polycycloalkyl aromatic compound, particularly dicyclohexylbenzene, with benzene to produce the monocycloalkyl aromatic analog, particularly monocyclohexylbenzene. The process is conducted in the presence of a catalyst comprising a Group IVB metal oxide modified with an oxyanion of a Group VIB metal oxide, TEA-mordenite, zeolite beta or a porous crystalline inorganic oxide material having an X-ray diffraction pattern including d-spacing maxima at 12.4±0.25, 6.9±0.15, 3.57±0.07 and 3.42±0.07 Angstrom.

Mixed metal oxide catalysts of the type comprising a Group IVB metal oxide modified with an oxyanion of a Group VIB metal oxide are described in, for example, U.S. Pat. No. 5,510,309, the entire contents of which are incorporated herein by reference. Preferably, the Group IVB metal oxide is an oxide of zirconium or titanium and the Group VIB metal oxyanion is an oxyanion of tungsten or molybdenum. Most preferably, the mixed metal oxide is an oxide of zirconium modified with an oxyanion of tungsten."

Zeolite beta is described in U.S. Pat. No. 3,308,069.

TEA-mordenite, i.e., synthetic mordenite prepared from a reaction mixture comprising a tetraethylammonium directing agent, is disclosed in U.S. Pat. Nos. 3,766,093 and 3,894,104. Small crystal TEA-mordenite having a crystal size less than 0.5 micron is disclosed in U.S. patent application Ser. No. 09/305,019 filed May 4, 1999.

Alternatively, the catalyst may comprise a porous crystalline inorganic oxide material having an X-ray diffraction pattern including d-spacing maxima at 12.4±0.25, 6.9±0.15, 3.57±0.07 and 3.42±0.07 Angstrom. The X-ray diffraction data used throughout this specification were obtained by standard techniques using the K-alpha doublet of copper as the incident radiation and a diffractometer equipped with a scintillation counter and associated computer as the collection system.

Suitable inorganic oxide materials are MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

The preferred catalyst is $WO_x/ZrO_2$.

The process of the invention is carried out by admixing benzene with the polycycloalkyl aromatic compound in a weight ratio of about 1:1 to 5:1, preferably 2:1 to 4:1. The mixture is then contacted with a catalyst as described above under reaction conditions including a temperature of about 100 to 300° C., a pressure of about 800 to 3500 kPa and a WHSV of about 1 to 10. Preferably, the reaction conditions including a temperature of about 130 to 250° C., a pressure of about 1500 to 2800 kPa and a WHSV of about 2 to 8.

The invention will now be more particularly described with reference to the accompanying Example.

EXAMPLE 1

A general procedure described here was followed to test catalysts for transalkylation of dicyclohexylbenzene with benzene. A catalyst containing 65 wt % zeolite Beta and 35 wt % alumina binder as 1/16" cylindrical extrudate was chopped to 1/16" length prior to use. One gram of this catalyst was diluted with sand to 3.0 cc and the catalyst/sand mixture was charged to a fixed-bed micro reactor with 3/8" outside diameter. The catalyst was dried with 100 cc/min of flowing nitrogen for 2 hours at 125° C. and 1 atm pressure. Nitrogen was turned off and the reactor pressure was set to 300 psig. A feed containing 75% of benzene and 25% of p-dicyclohexylbenzene by weight was introduced to the reactor through a syringe pump at 60 cc/hour for 1 hr while the reactor was ramped to the desired temperature. The feed rate was then reduced to 4.0 WHSV for the test run. Liquid products were collected in a cold product trap and analyzed off-line. The results are summarised in Table 1.

The above procedure was repeated with catalysts containing $WO_x/ZrO_2$, TEA-mordenite and MCM-22. Again the results are summarised in Table 1.

TABLE 1

| Catalyst | $WO_x/ZrO_2$ | TEA-Mordenite | Beta | MCM-22 |
|---|---|---|---|---|
| Binder | None | 35% alumina | 35% alumina | 35% alumina |
| Days on Stream | 1.1 | 3.7 | 2.8 | 3.8 |
| Temperature, ° C. | 150 | 170 | 180 | 195 |
| p-Dicyclo-hexylbenzene Conversion, % | 63.0 | 46.8 | 47.0 | 41.1 |

TABLE 1-continued

| Catalyst | $WO_x/ZrO_2$ | TEA-Mordenite | Beta | MCM-22 |
|---|---|---|---|---|
| Selectivity, wt % | | | | |
| Lights | 0.227 | 0.030 | 0.047 | 0.039 |
| Methylcyclo-pentane | 0.442 | 0.022 | 0.024 | 0.205 |
| Cyclohexane | 0.091 | 0.138 | 0.428 | 0.086 |
| Toluene | 0.028 | 0.000 | 0.028 | 0.000 |
| Other $C_{12}$ compounds | 1.609 | 5.927 | 5.852 | 6.497 |
| Phenylcyclo-hexane | 96.640 | 93.437 | 92.769 | 92.675 |
| Other $C_{18}$ compounds | 0.963 | 0.446 | 0.853 | 0.498 |
| Sum | 100.00 | 100.00 | 100.00 | 100.00 |

It will be seen that the $WO_x/ZrO_2$ catalyst was very active for this reaction and gave phenylcyclohexane with high selectivity.

What is claimed is:

1. A process for the transalkylation of a polycycloalkyl aromatic compound comprising the step of contacting the polycycloalkyl aromatic compound with benzene to produce a monocycloalkyl aromatic compound in the presence of a catalyst selected from the group consisting of an acidic solid comprising Group IVB metal oxide modified with an oxyanion of a Group VIB metal oxide, TEA-mordenite, and zeolite beta.

2. The process of claim 1 wherein the polycycloalkyl aromatic compound is dicyclohexylbenzene.

3. The process of claim 1 wherein said acidic solid is an oxide of zirconium modified with an oxyanion of tungsten.

4. The process of claim 1 wherein the contacting step is conducted at a temperature of about 100 to 300° C., a pressure of about 800 to 3500 kPa, a WHSV of about 1 to 10 and a weight ratio of benzene to polycycloalkyl aromatic compound of about 1:1 to 5:1.

5. The process of claim 1 wherein the contacting step is conducted at a temperature of about 130 to 250° C., a pressure of about 1500 to 2800 kPa, a WHSV of about 2 to 8 and a weight ratio of benzene to polycycloalkyl aromatic compound of about 2:1 to 4:1.

6. The process of claim 1 wherein said catalyst is an acidic solid comprising a Group IVB metal oxide modified with an oxyanion of a Group VIB metal oxide.

7. The process of claim 1 wherein said catalyst is selected from the group consisting of TEA-mordenite and zeolite beta.

8. The process of claim 1 wherein said catalyst is TEA-mordenite.

9. The process of claim 1 wherein said catalyst is zeolite beta.

* * * * *